(12) United States Patent
Peake

(10) Patent No.: US 9,867,563 B2
(45) Date of Patent: Jan. 16, 2018

(54) REDUCED COGNITIVE FUNCTION DETECTION AND ALLEVIATION SYSTEM FOR A PILOT

(71) Applicant: Carleton Life Support Systems, Inc., Davenport, IA (US)

(72) Inventor: Steven C. Peake, Dubuque, IA (US)

(73) Assignee: Carleton Life Support Systems Inc., Davenport, IA (US)

( * ) Notice: Subject to any disclaimer, the term of this patent is extended or adjusted under 35 U.S.C. 154(b) by 277 days.

(21) Appl. No.: 14/594,877

(22) Filed: Jan. 12, 2015

(65) Prior Publication Data
US 2015/0196245 A1 Jul. 16, 2015

Related U.S. Application Data

(60) Provisional application No. 61/925,807, filed on Jan. 10, 2014.

(51) Int. Cl.
*A61B 3/11* (2006.01)
*A61B 5/18* (2006.01)
(Continued)

(52) U.S. Cl.
CPC ............... *A61B 5/18* (2013.01); *A61B 3/112* (2013.01); *A62B 7/14* (2013.01); *A61M 16/0003* (2014.02); *A61M 16/0051* (2013.01)

(58) Field of Classification Search
CPC .......... A61M 16/0003; A61M 16/0027; A61M 16/0051; A61B 5/18; A61B 3/112; A62B 7/14
See application file for complete search history.

(56) References Cited

U.S. PATENT DOCUMENTS 3,521,627 A * 7/1970 Murray .................... A62B 7/14
128/202.27
4,960,119 A * 10/1990 Hamlin .................... A62B 7/14
128/201.25
(Continued)

OTHER PUBLICATIONS

United States Air Force Scientific Advisory Board Sab: "Report on Aircraft Oxygen Generation", Feb. 1, 2012, XP055413510, Retrieved Oct. 9, 2017, http://www.airforcemag.com/DocumentFile/Documents/2012/AFSAB_Oxygen_020112.pdf.
(Continued)

*Primary Examiner* — Valerie L Woodward
(74) *Attorney, Agent, or Firm* — Woods Oviatt Gilman LLP; Katherine H. McGuire, Esq.

(57) ABSTRACT

A system for detecting and alleviating pilot hypoxia is provided. The system includes an oxygen generator adapted to be powered by a power supply. The oxygen generator is in communication an oxygen delivery device where the oxygen delivery device is adapted to deliver supplemental oxygen to a pilot. A control module is in communication with the oxygen generator and the power supply. A hypoxia detection device is in communication with the control module wherein the control module causes one or both of the oxygen generator and the oxygen delivery device to increase an amount of oxygen being delivered to the pilot upon detection of pilot hypoxia. The hypoxia detection device may include a pupillometer and a luminometer and/or a flash generator.

16 Claims, 3 Drawing Sheets

(51) Int. Cl.
*A62B 7/14* (2006.01)
*A61M 16/00* (2006.01)

(56) References Cited

U.S. PATENT DOCUMENTS

| | | | |
|---|---|---|---|
| 2003/0218719 A1* | 11/2003 | Abourizk | G06K 9/00597 351/209 |
| 2003/0233936 A1 | 12/2003 | Crome | |
| 2006/0203197 A1* | 9/2006 | Marshall | A61B 3/112 351/246 |
| 2007/0120691 A1* | 5/2007 | Braun | B60K 28/063 340/576 |
| 2009/0018419 A1* | 1/2009 | Torch | A61B 3/0066 600/318 |
| 2010/0012116 A1 | 1/2010 | Rittner et al. | |
| 2010/0024821 A1 | 2/2010 | Rittner et al. | |
| 2011/0000490 A1 | 1/2011 | Gillotin et al. | |
| 2012/0050516 A1* | 3/2012 | Tsukizawa | G06K 9/00604 348/78 |
| 2012/0069301 A1* | 3/2012 | Hirata | A61B 3/112 351/209 |

OTHER PUBLICATIONS

Klingner, Jeff, Measuring Cognitive Load uring Visual Tasks by Combining Pupillometry and Eye Tracking, May 1, 2010, XP055256289, Retrieved Mar. 8, 2016, http://graphics.stanford.edu/papers/klingner-dissertation/klingner-lissertation.pdf.

Schnell, Thomas, et al., "The Cognitive Pilot Helmet: enabling pilot-aware smart avionics", Proceedings vol. 9025 IS&T/SPIE Electronic Imaging, Feb. 2-6, 2014 Intelligent Robots and Computer Vision XXXI: Algorithms and Techniques, vol. 7326, Apr. 30, 2009, p. 73260A, XP055413448, ISSN: 0277-786X, DOI: 10.1117/12.820300.

* cited by examiner

REDUCED COGNITIVE FUNCTION DETECTION AND ALLEVIATION SYSTEM FOR A PILOT

This Application claims the benefit of U.S. Provisional Application No. 61/925,807 filed Jan. 10, 2014.

BACKGROUND OF THE INVENTION

The present invention relates to a hypoxia detection and alleviation system, and more particularly to a hypoxia detection and alleviation system to be used by a pilot of an aircraft, and even more particularly to a hypoxia detection and alleviation system utilizing pupillometry to monitor one or both pupils of the pilot, and most particularly to a hypoxia detection and alleviation system coupled to an onboard oxygen system (wherein the oxygen system is configured to provide a higher dosage of oxygen to the pilot upon detection of hypoxic stress. While described herein as a system for detecting and alleviating hypoxia, it should be understood by those skilled in the art that the present system can be used to detect and alleviate additional causes of reduced cognitive function that may be experienced by a pilot. Additionally, the onboard oxygen system may be a stored supply of supplemental oxygen, such as a storage tank filled with oxygen gas or liquid oxygen, or may include an onboard oxygen generating system commonly referred to as OBOGS.

Hypoxia reports regarding aircraft pilots continue to gain significant attention, including those involved with military fighter aircraft such as the F-22 and F-35 as well as private and commercial non-military aircraft. Pilots are routinely exposed to altitudes that are significantly higher than sea level. These high altitudes reduce the partial pressure of oxygen in their lungs. In extreme cases the reduced partial pressure of oxygen deprives the crew and passengers of adequate oxygen supply leading to hypoxia. Early symptoms of hypoxia may include light-headedness, fatigue and nausea. Prolonged exposure to reduced oxygen or a more rapid onset of hypoxia (such as may be encountered during aviation) can lead to confusion, disorientation, severe headaches, and may even lead to death. Studies by the US military have demonstrated that for normal, healthy individuals, significant physiological responses occur at altitudes greater than about 10,000 feet above sea level (ASL) while other studies have shown that a reduction in night vision and mild hypoxia can occur at altitudes as low as 5,000 feet ASL. Additionally, as a person ages, his or her susceptibility to hypoxia varies widely.

To account for the reduced oxygen and possibility of a hypoxic event at high altitudes, aircraft are generally pressurized (commercial airliners) or include supplemental oxygen, such as supplemental oxygen tanks or an onboard oxygen gas generation system (OBOGS), either of which may supply the pilot with oxygen enriched gas through a gasmask worn by the pilot when at high altitudes. Nevertheless, risks of hypoxia still remain. Research has shown that there exists a clear link between pupil size and the early effects of hypoxia. Indeed, it has been found that the eyes may be the first indicators of the onset of hypoxia, either through loss of peripheral vision, change in color perception or other optical anomalies. Basic functions of the eye can be measured through the size and response of the pupil and this response can be measured non-invasively using a technique known as pupillometry. The measurement of the pupil size and/or response provides a valid means to detect the early effects of hypoxia.

Thus, what is needed is a hypoxia detection and alleviation device that may monitor pilots and detect early indications of hypoxia so that the pilot (or the oxygen system/OBOGS through automatic control by the aircraft's control system) may take corrective actions to alleviate the conditions leading to hypoxia, such as lowering altitude or increasing the partial pressure of oxygen being supplied to the pilot.

SUMMARY OF THE INVENTION

The present invention addresses the above needs by providing a reduced cognitive function detection and alleviation system, and more particularly for a reduced cognitive function detection and alleviation system which utilizes a pupillometer to monitor the pilot's eyes for indications of possible reduced cognitive function. The pupillometer is coupled to the aircraft's onboard oxygen generation system so as to cause the supplemental oxygen system to supply additional oxygen to the pilot to alleviate reduced cognitive function symptoms.

In an embodiment of the present invention, a system for detecting and alleviating pilot reduced cognitive function is provided. The system comprises an oxygen supply system adapted to be actuated by a power supply. The oxygen supply system is in communication an oxygen delivery device where the oxygen delivery device is adapted to deliver supplemental oxygen to a pilot. A control module is in communication with the oxygen supply system and the power supply. A reduced cognitive function detection device is in communication with the control module wherein the control module causes one or both of the oxygen supply system and the oxygen delivery device to increase an amount of oxygen being delivered to the pilot upon detection of pilot reduced cognitive function.

In a further aspect of the present invention, the reduced cognitive function is indicative of hypoxia or hypoxic stress.

In still a further aspect of the present invention, the oxygen supply system is an onboard stored oxygen supply of high purity gaseous or liquid oxygen.

In a further aspect of the present invention, the oxygen generator is an onboard oxygen generating system (OBOGS). And still further the OBOGS is either a pressure swing adsorption device or a vacuum pressure swing adsorption device. A compressor may be powered by the power source wherein the compressor supplies pressurized air to the pressure swing adsorption device or the vacuum pressure swing adsorption device. A plenum may be positioned between the oxygen generator and the oxygen delivery device. The plenum may include a pressure sensor in communication with the control module wherein the control module regulates power to the oxygen generator to maintain a substantially constant gas pressure within the plenum.

In another aspect of the present invention, the reduced cognitive function detection device comprises a pupillometer configured to monitor a pupil size of the pilot. The control module of the reduced cognitive function detection device may include a data file containing pilot pupil size data as a function of ambient light. The reduced cognitive function detection device may further comprise a luminometer configured to monitor an ambient light level wherein pilot pupil size is compared to the data file at the ambient light level so that a pupil size outside the pilot pupil size data indicates reduced cognitive function.

In still another aspect of the present invention, the reduced cognitive function detection device further may comprise a flash generator configured to emit a flash of light wherein changes to pilot pupil size are monitored by the pupillometer. In one aspect, the flash generator emits a flash of light at a user-selected time interval prior to the pupillometer monitoring the pupil response to detect pilot reduced cognitive function. The flash of light is emitted for less than one second and the user-selected time interval between light emissions is about 15 to about 30 seconds. In another aspect, the flash generator emits a flash of light at after the pupillometer detects pilot reduced cognitive function wherein the pupillometer again monitors the pupil response so as to confirm pilot reduced cognitive function.

In yet another aspect of the present invention, a method for detecting and alleviating pilot reduced cognitive function is provided. The method comprises providing a system for detecting and alleviating pilot reduced cognitive function comprising an oxygen supply system adapted to be powered by a power supply. The oxygen supply system is in communication with an oxygen delivery device where the oxygen delivery device is adapted to deliver supplemental oxygen to a pilot. A control module is in communication with the oxygen supply system and the power supply. A reduced cognitive function detection device is in communication with the control module wherein the control module initiates an increase in oxygen being delivered to the pilot upon detection of pilot reduced cognitive function. The step further comprises monitoring a pupil of the pilot using the reduced cognitive function detection device to detect the pilot reduced cognitive function; allowing the reduced cognitive function detection device to communicate a control signal to the control module upon the occurrence of pilot reduced cognitive function; and allowing the control module to communicate a control signal to one or both of the oxygen delivery device and oxygen supply system to increase the oxygen being delivered to the pilot.

In a further aspect of the method, the reduced cognitive function detection device comprises a pupillometer for monitoring the pupil of the pilot. The reduced cognitive function detection device may further comprise a luminometer configured to measure ambient light levels. The monitoring of the pupil by the pupillometer is compared to a data file having a baseline pupil measurement at the measured ambient light level to detect pilot reduced cognitive function.

In still a further aspect of the method, the reduced cognitive function detection device further comprises a flash generator configured to emit a flash of light wherein the pupillometer monitors pupil response to detect pilot reduced cognitive function. In one aspect, the flash generator emits a flash of light at a user-selected time interval prior to the pupillometer monitoring the pupil response to detect pilot reduced cognitive function. The flash of light is emitted for less than one second and the user-selected time interval between light emissions is about 15 to about 30 seconds. In another aspect, the flash generator emits a flash of light at after the pupillometer detects pilot reduced cognitive function wherein the pupillometer again monitors the pupil response so as to confirm pilot reduced cognitive function.

BRIEF DESCRIPTION OF THE DRAWINGS

The invention will further be described, by way of example, with reference to the accompanying drawings.

DETAILED DESCRIPTION

Figure 1:
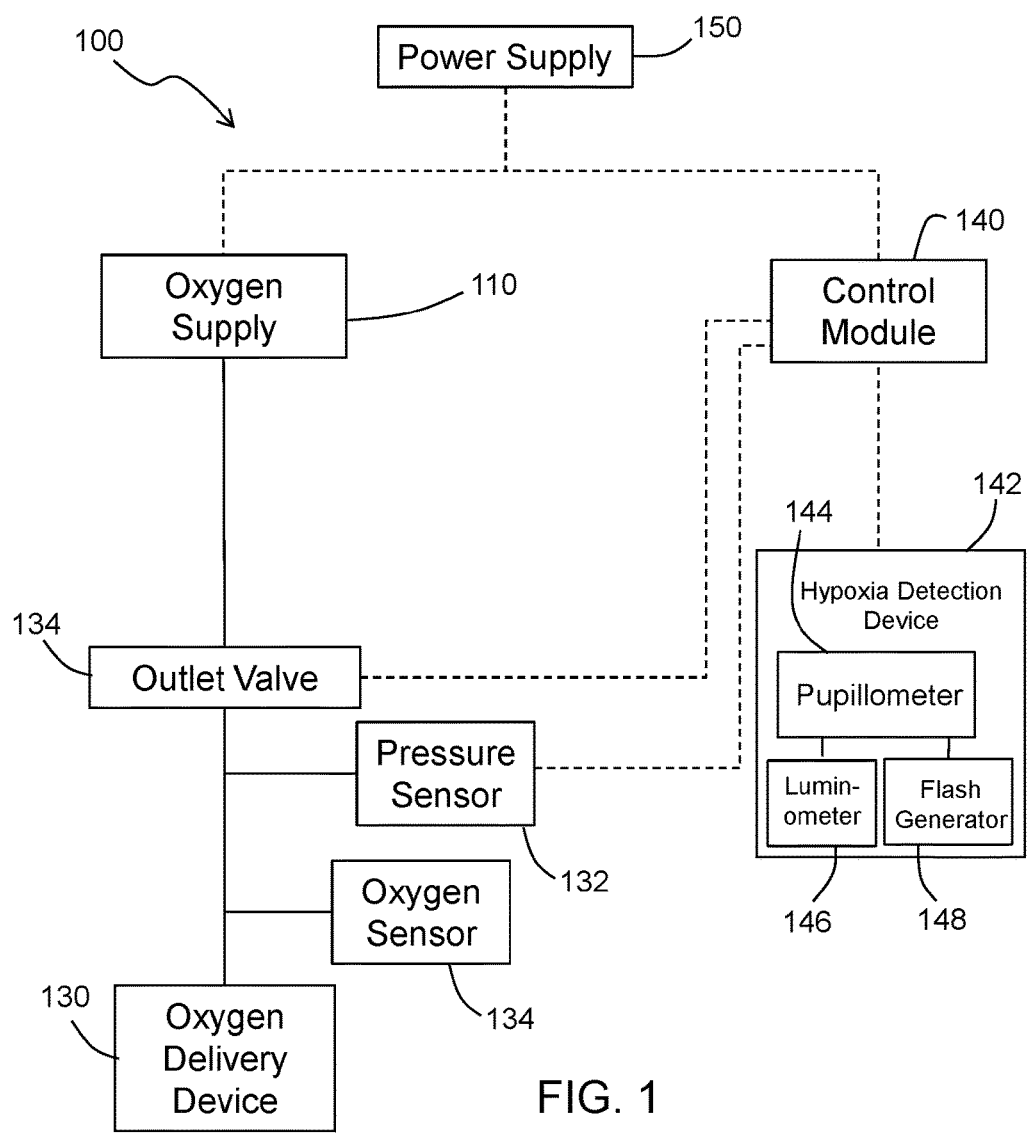
FIG. 1 is a schematic view of a first embodiment of a hypoxia detection and alleviation system in accordance with the present invention.
Figure 1A:
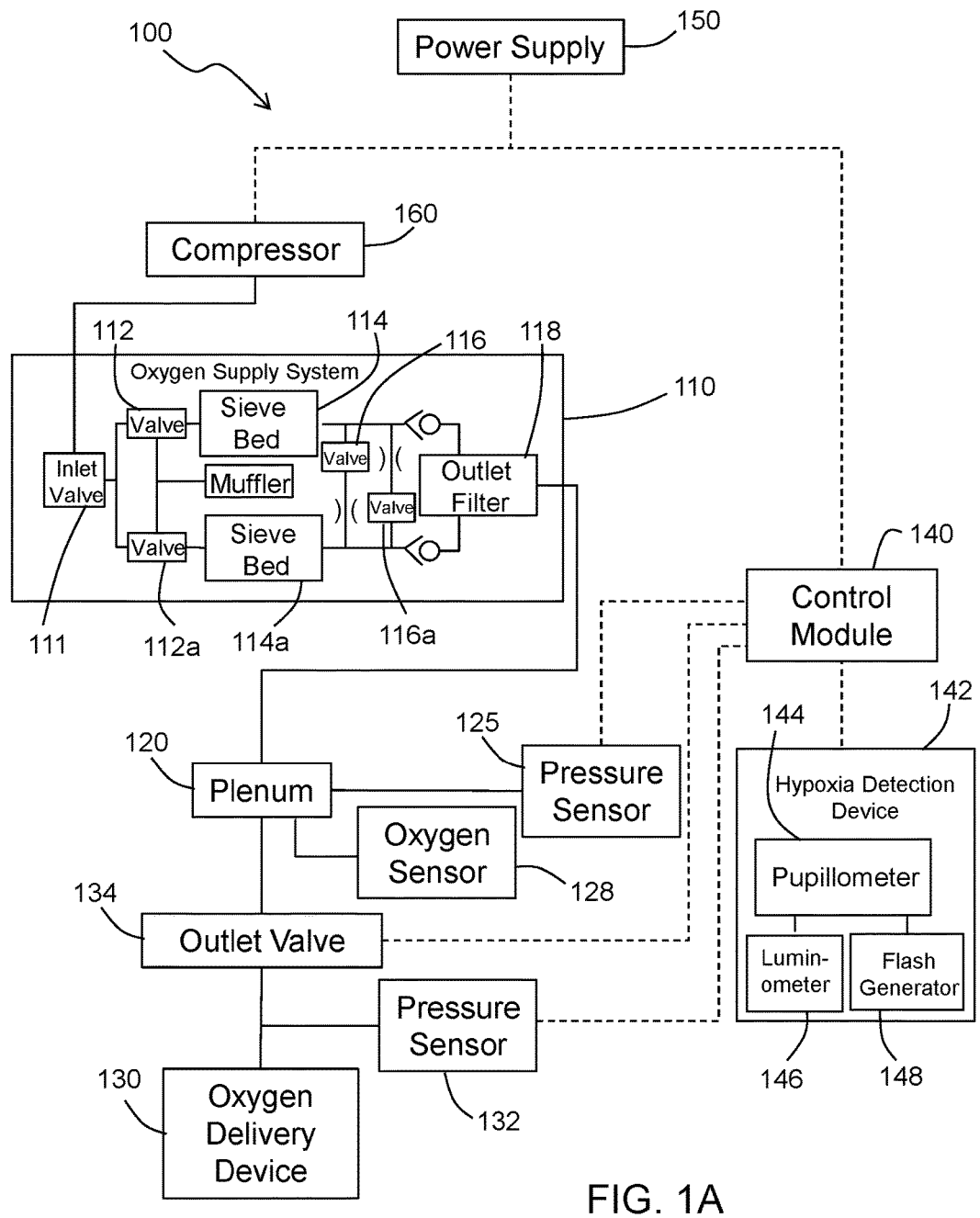
FIG. 1A is a schematic view of a second embodiment of a hypoxia detection and alleviation system in accordance with the present invention

An embodiment of a reduced cognitive function detection and alleviation system for use in aviation in accordance with the present invention is shown in FIGS. 1 and 1A and is generally indicated by reference numeral 100. For sake of simplicity, reduced cognitive function detection and alleviation system 100 will be described herein as hypoxia detection and alleviation system 100. However, while described hereinafter as a system for detecting and alleviating hypoxia, it should be understood by those skilled in the art that the present system can be used to detect and alleviate additional causes of reduced cognitive function that may be experienced by a pilot. The detection and alleviation of these additional causes of reduced cognitive function are to be considered by those skilled in the art as incorporated in the teachings of the present invention. Thus, while the following description will be directed toward detecting and alleviating hypoxia and hypoxic stress, it should be understood that this description would equally apply to the detection and alleviation of any amenable cause of reduced cognitive function.

As shown in FIG. 1, hypoxia detection and alleviation system 100 is generally comprised of an oxygen supply system 110 powered by a power supply 150 under operational control of a control module 140. Power supply 150 may be the onboard power of an aircraft wherein the oxygen supply system is plugged into the aircraft power supply. Alternatively, power supply 150 further includes a back-up battery unit, and in accordance with a further aspect of the present invention, includes a rechargeable battery unit. Oxygen supply system 110 may be a stored oxygen supply, such as a canister of high purity (greater than about 95% oxygen) gaseous or liquid oxygen, wherein supplemental oxygen is selectively delivered to the pilot by actuation of a canister valve via power supply 150 upon receipt of a control signal from control module 140. Additionally or alternative, oxygen supply 110 may be any suitable oxygen generator, such as a pressure swing adsorption, vacuum pressure swing adsorption, or electrochemical device. In accordance with an embodiment of the present invention, and as shown in FIG. 1A, oxygen supply system 110 is a pressure swing adsorption (PSA) oxygen generator having an inlet valve 111 to throttle incoming air to the generator. The PSA oxygen generator may be equipped with a pair of molecular sieve beds 114/114a. Bed valves 112/112a selectively direct compressed inlet air from inlet valve 111 to one or the other of sieve beds 114/114a such that high pressure inlet air is directed to only one sieve bed at a time. Control of each of the valves is monitored, and change states initiated, by control module 140 (control pathways not shown for sake of clarity).

In operation, each sieve bed 114/114a includes a zeolite which selectively adsorbs nitrogen gas at high pressure such that an enriched oxygen gas is produced for eventual supply to oxygen delivery devices 130 after passing through an optional outlet filter 118. As the selected sieve bed is being pressurized with inlet air, active sites on the zeolites adsorb nitrogen until the zeolite bed is saturated with nitrogen and oxygen enrichment efficiency is minimized. At this point, the status of bed valves 112/112a is reversed such that compressed inlet air is delivered to the second of the two sieve beds 114/114a. The nitrogen-rich, previously pressurized bed is then allowed to depressurize, thereby desorbing the nitrogen from the zeolite, with the nitrogen-rich gas being exhausted from oxygen supply system 110. In accordance with an aspect of the present invention, the PSA oxygen generator includes post-bed pressure equalizing valves 116/116A to increase system efficiencies as is known in the art. In this manner, oxygen enriched air may be continually produced as one sieve bed adsorbs nitrogen to produce the oxygen enriched air while the other sieve bed is being depressurized so as to desorb nitrogen and regenerate the zeolite active sites for another pressurization cycle.

For PSA systems to operate properly, an inlet supply of compressed air is required. In one embodiment of the present invention, it is envisioned that such compressed air is delivered as conditioned engine bleed air from a gas turbine engine (such as those used in military aircraft). Alternatively, for general aviation aircraft that are powered by reciprocating engines which do not produce an inherent compressed gas supply for the oxygen supply system, hypoxia detection and alleviation system 100 may further include a compressor 160 adapted to compress ambient air, such as cabin air, for passage into oxygen supply system 110. An optional inline filter (not shown) may further be positioned at the compressor air inlet so as to remove any particulate material, water vapor or other harmful materials from the air supply before directing the pressurized air into the oxygen generator.

Oxygen produced by oxygen supply system 110 may be directed to a plenum 120 for eventual delivery to an oxygen delivery device 130. Coupled to plenum 120, and in communication with control module 140, is plenum pressure sensor 125. Plenum pressure sensor 125 monitors the gas pressure within the plenum 120 and sends a control signal to the control module 140 wherein the control module 140 may regulate the compressor speed of compressor 160 so as to maintain a substantially constant plenum pressure. An oxygen sensor 128 is further coupled to the plenum and monitors the oxygen concentration of the supply gas stored within the plenum. Should the OBOGS 110 receive a control signal to increase oxygen throughput (such as during a reduced cognitive function detection), the increased oxygen production of the OBOGS will be reflected by an increase oxygen concentration in the plenum as monitored by oxygen sensor 128. (Similarly, as shown in FIG. 1, for those systems using stored canister oxygen, oxygen sensor 134 monitors oxygen concentration being supplied to oxygen delivery device 130 so as to ensure opening of the canister valve and subsequent delivery of high purity oxygen to the pilot). While shown as a single oxygen delivery device 130, it is envisioned that any number of oxygen delivery devices may be employed provided that sufficient oxygen may be generated and delivered to each device under normal operating conditions. In accordance with an aspect of the present invention, oxygen delivery device 130 may be either a mask, nasal cannula or both.

To increase oxygen generator efficiencies, oxygen delivery device 130 may include a pressure sensor 132 and outlet valve 134 so as to enable pulsed dosing. That is, pressure sensor 132 is configured to monitor a wearer's breathing. When an individual is about to inhale, the individual's diaphragm drops causing a decrease in pressure in the lungs. This decrease in pressure is detected by pressure sensor 132. Upon detecting a pressure decrease, pressure sensor 132 signals outlet valve 134 to open so as to deliver a metered dose of oxygen to the oxygen delivery device 130. As such, the oxygen delivery is pulsed such that oxygen is supplied only when an inhalation is imminent. In this manner, the amount of oxygen needed to be generated by oxygen supply system 110 is reduced, thereby requiring less power to drive the generator, thus leading to a prolonged usable battery charge, prolonged lifetime of the zeolite beds and increased overall system efficiencies. In accordance with an aspect of the present invention, oxygen delivery device 130 may also include an independent indicator of oxygen flow. Examples of suitable flow indicators may include, but are not limited to, ball, wheel or paddle style visual indicators. This independent flow indication provides visual confirmation to the end user that the oxygen is being successfully delivered from oxygen supply system 110 through oxygen delivery device 130.

Control module 140 may be further coupled to additional operational modalities related to hypoxia detection and alleviation system 100. For instance, hypoxia detection device 142 may be coupled to control module 140. For military style fighters, hypoxia detection device 142 may be mounted within the pilot's helmet while private and commercial aircraft may have the hypoxia detection device 142 mounted within the cockpit. Hypoxia detection device 142 generally includes a pupillometer 144 which is configured to monitor pupil size of the pilot. In accordance with one aspect of the present invention, pupillometer 144 is selected so as to enable pupil tracking while the eyes are in motion. Hypoxia detection device 142 may further include provision of a luminometer 146 used to measure ambient light. In accordance with an aspect of the present invention, a relationship between pupil size and background lumens for each pilot may be compiled so as to establish a pupil size baseline over light conditions likely to be encountered by pilots during flight. This baseline data may then be digitally stored within memory located within the pilot's helmet or the aircraft's onboard computer. With this baseline, hypoxia detection device 142 may monitor pupil size for changes outside this baseline (or a defined range based thereon) where such deviations may be indicative of hypoxic stress. Should hypoxic stress be indicated, hypoxia detection device 142 may then send a control signal to control module 140 so that control module 140 may send appropriate control signals to the compressor 160 and/or outlet valve 134 to thereby increase oxygen supply to the pilot. This increase in oxygen may be either through an increase in flow of OBOGS gas or through increasing the concentration of oxygen in the OBOGS gas being supplied to the pilot, or both.

In accordance with a further aspect of the present invention, hypoxia detection device 142 may include a flash generator 148 configured to emit sub-second flashes of light. Pupillometer 144 then measures the pupil response to such a flash as it has been shown that pupil size response rates to changing light intensities correlate to levels of hypoxic stress. To avoid unwanted distractions to the pilot, flash generator 148 may emit flashes having frequencies near the edge of the visual frequency range or beyond the visual range including infrared or ultraviolet light frequencies. Additionally or alternatively, the light flash may be of relatively small intensity difference compared to ambient light so that such a flash is consciously imperceptible to the pilot while also being sufficient to generate the pupil response needed to interrogate the possibility of hypoxic stress. Flash generator 148 may either provide constant monitoring, such as by emitting the flash of light at a selected time interval (i.e. every 15-30 seconds), or may be initiated after pupillometer 144 detects possible hypoxia wherein the flash generator operates to confirm or provide additional indications of hypoxic stress. In this manner, if the steady state pupil size correlation does not suggest stress, no "flashing" would be required. However, should stress be suspected, then a change of light intensity would be introduced looking for pupil response as a means of verification of hypoxic stress.

Beyond monitoring for pilot hypoxia, hypoxia detection device 142 may also indicate other pilot conditions. By way of example, by monitoring the pilot's pupils. Hypoxia detection device 142 may record the blink rate of the pilot. A significant change in blink rate may be indicative of a change in the pilot's mental acuity such as due to drowsiness or other similar condition. As a further example, hypoxia detection device 142 may also serve to indicate other consciousness affecting conditions such as CO contamination in the pilot's breathing air stream. As described above, if any of these adverse conditions is detected, hypoxia detection device 142 may provide a control signal to control module 140 wherein additional oxygen is provided to the pilot in an attempt to alleviate these conditions.

Figure 2:
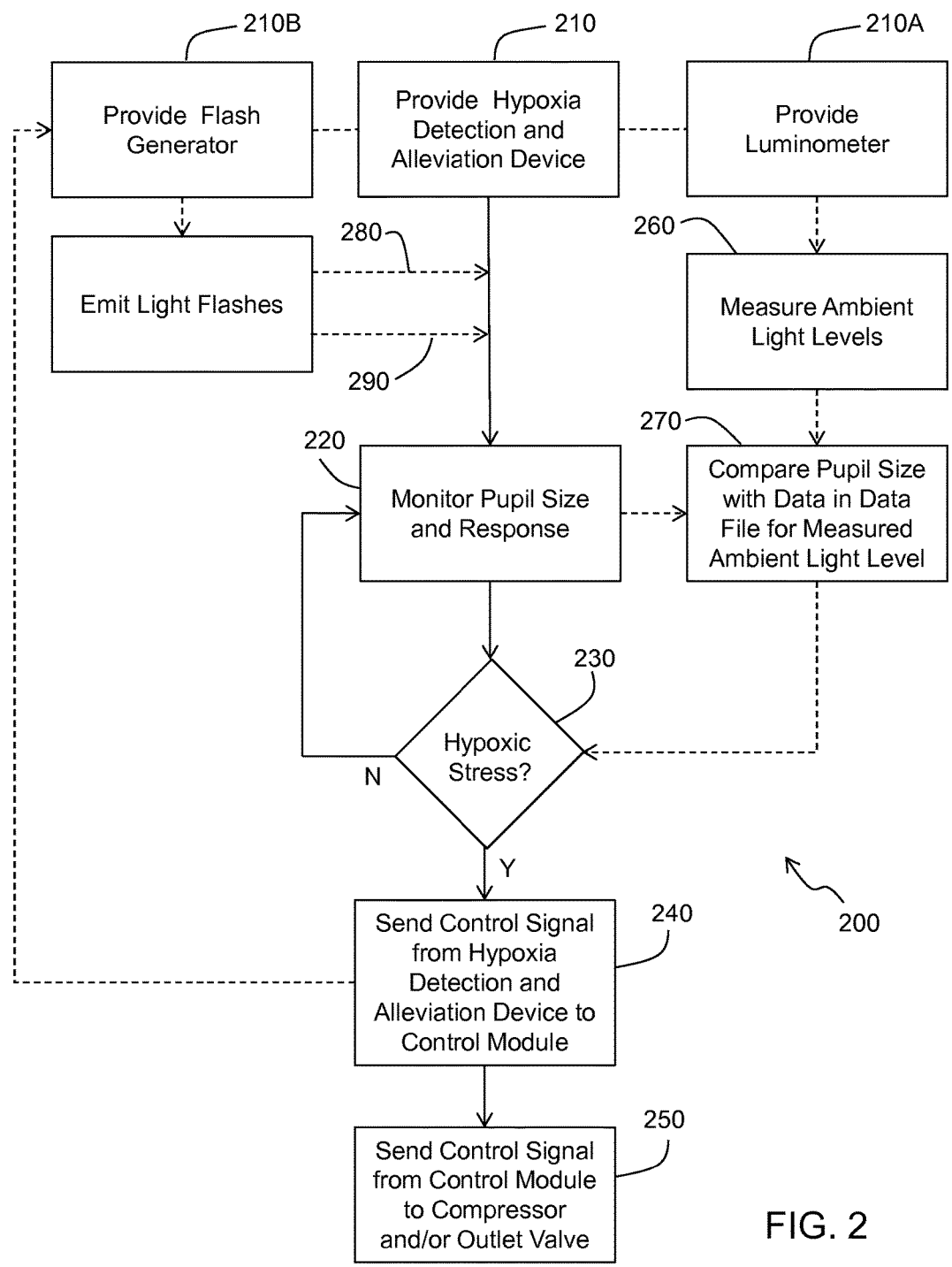
FIG. 2 is a flowchart for a method of detecting and alleviating pilot hypoxia using a hypoxia detection and alleviation system in accordance with the present invention.

In accordance with a further aspect of the invention, a method 200 of detecting and alleviating pilot hypoxia is provided. As shown in FIG. 2, step 210 comprises equipping a pilot with a hypoxia detection and alleviation device such as device 100 described above with regard to FIG. 1. Hypoxia detection and alleviation device 100 includes a pupillometer such as pupillometer 144 which, in step 220, monitors the pupil size and response of the pilot for indications of hypoxic stress. At step 230, if hypoxic stress is not detected, hypoxia detection and alleviation device 100 continues to monitor the pilot's pupils. If hypoxic stress is detected, a control signal is communicated to a control module (such as control module 140) in step 240. Control module 140, in step 250, the sends a control signal to compressor 160 and/or outlet valve 134 to increase oxygen supply to the pilot. Again, this increase in oxygen may be either through an increase in flow of OBOGS gas or through increasing the concentration of oxygen in the OBOGS gas being supplied to the pilot, or both.

Hypoxia detection and alleviation device 100 may further include provision 210A of a luminometer, such as luminometer 146. Luminometer 146 measures ambient light at step 260. With the ambient light level measures, in step 270, the pilot's pupil size as monitored by the pupillometer in step 220 is compared with a data file containing pilot pupil size data as a function of ambient light wherein the data file is digitally stored within memory located within the pilot's helmet or the aircraft's onboard computer. The comparison will then be used as an indication of hypoxic stress in step 230.

As described above, hypoxia detection and alleviation device 100 may further include provision 210B of a flash generator, such as flash generator 148. Flash generator 148 may be operated in various modes, including constant monitoring and selected monitoring. If programmed for constant monitoring, step 280 comprises flash generator 148 emitting a light flash at a user-selected time interval prior to the pupillometer monitoring pupil size and response (step 220). As described above, this flash of light is generally less than a second in duration and may be repeated about every 15-30 seconds. Additionally and/or alternatively should hypoxic stress be indicated by the pupillometer (step 230), at step 290, flash generator 148 may be instructed by control module 140 to emit a flash of light wherein the pilot's pupil response is monitored (step 220) such that flash generator 148 provided additional confirmation of a hypoxic stress condition.

Although the invention has been described with reference to preferred embodiments thereof, it is understood that various modifications may be made thereto without departing from the full spirit and scope of the invention as defined by the claims which follow.

What is claimed is:

1. A system for detecting and alleviating reduced cognitive function of a pilot, the system comprising:
    a) an oxygen supply system adapted to be actuated by a power supply, the oxygen supply system in communication with an oxygen delivery device, the oxygen delivery device adapted to deliver supplemental oxygen to a pilot,
    b) a control module in communication with the oxygen supply system and the power supply; and
    c) a reduced cognitive function detection device comprising a pupillometer configured to monitor a pupil size of the pilot, the reduced cognitive function detection device in communication with the control module wherein the control module includes a data file containing compiled pilot pupil size data as a function of ambient light and wherein the reduced cognitive function detection device further comprises a luminometer configured to measure an ambient light level wherein pilot pupil size is compared to the data file at the ambient light level so that a pupil size outside the pilot pupil size data indicates reduced cognitive function and wherein the control module causes one or both of the oxygen supply system and the oxygen delivery device to increase an amount of oxygen being delivered to the pilot upon detection of pilot reduced cognitive function.

2. The system for detecting and alleviating reduced cognitive function of a pilot of claim 1 wherein the reduced cognitive function is indicative of hypoxia or hypoxic stress.

3. The system for detecting and alleviating reduced cognitive function of a pilot of claim 1 wherein the oxygen supply system is an onboard stored oxygen supply of high purity gaseous or liquid oxygen.

4. The system for detecting and alleviating reduced cognitive function of a pilot of claim 1 wherein the oxygen supply system is an onboard oxygen generating system (OBOGS).

5. The system for detecting and alleviating reduced cognitive function of a pilot of claim 4 wherein the OBOGS is either a pressure swing adsorption device or a vacuum pressure swing adsorption device.

6. The system for detecting and alleviating reduced cognitive function of a pilot of claim 5 and further comprising a compressor powered by the power source wherein the compressor supplies pressurized air to the pressure swing adsorption device or the vacuum pressure swing adsorption device.

7. The system for detecting and alleviating reduced cognitive function of a pilot of claim 4 further comprising a plenum between the oxygen supply system and the oxygen delivery device, the plenum including a pressure sensor in communication with the control module wherein the control module regulates power to the OBOGS to maintain a substantially constant gas pressure within the plenum.

8. The system for detecting and alleviating reduced cognitive function of a pilot of claim 1 wherein the reduced cognitive function detection device further comprises a flash generator configured to emit a flash of light wherein changes to pilot pupil size are monitored by the pupillometer.

9. The system for detecting and alleviating reduced cognitive function of a pilot of claim 8 wherein the flash generator emits a flash of light at a user-selected time interval prior to the pupillometer monitoring the pupil response to detect reduced cognitive function of the pilot.

10. The system for detecting and alleviating reduced cognitive function of a pilot of claim 9 wherein the flash of light is emitted for less than one second and the user-selected time interval between light emissions is about 15 to about 30 seconds.

11. The system for detecting and alleviating reduced cognitive function of a pilot of claim 8 wherein the flash generator emits a flash of light after the pupillometer detects reduced cognitive function of the pilot wherein the pupillometer again monitors the pupil response so as to confirm reduced cognitive function of the pilot.

12. A method for detecting and alleviating reduced cognitive function of a pilot, comprising:
  a) providing a system for detecting and alleviating reduced cognitive function of a pilot comprising:
    i) an oxygen supply system adapted to be actuated by a power supply, the oxygen supply system in communication with an oxygen delivery device, the oxygen delivery device adapted to deliver supplemental oxygen to a pilot,
    ii) a control module in communication with the oxygen supply system and the power supply; and
    iii) a reduced cognitive function detection device comprising a pupillometer configured to monitor a pupil size of the pilot, the reduced cognitive function detection device in communication with the control module wherein the control module includes a data file containing compiled pilot pupil size data as a function of ambient light and wherein the reduced cognitive function detection device further comprises a luminometer configured to measure an ambient light level;
  b) monitoring the pupil size of the pilot using the pupillometer;
  c) measuring the ambient light level using the luminometer;
  d) comparing the monitored pupil size to the compiled pilot pupil size data corresponding to the measured ambient light level to detect an occurrence of reduced cognitive function;
  e) communicating via the reduced function detection device a pupillometer control signal to the control module upon the occurrence of reduced cognitive function of the pilot; and
  f) communicating via the control module a control module control signal to one or both of the oxygen delivery device and oxygen supply system to increase the oxygen being delivered to the pilot.

13. The method for detecting and alleviating reduced cognitive function of a pilot of claim 12 wherein the reduced cognitive function detection device further comprises a flash generator configured to emit a flash of light wherein the pupillometer monitors pupil response to detect reduced cognitive function of the pilot.

14. The method for detecting and alleviating reduced cognitive function of a pilot of claim 13 wherein the flash generator emits a flash of light at a user-selected time interval prior to the pupillometer monitoring the pupil response to detect reduced cognitive function of the pilot.

15. The method for detecting and alleviating reduced cognitive function of a pilot of claim 14 wherein the flash of light is emitted for less than one second and the user-selected time interval between light emissions is about 15 to about 30 seconds.

16. The method for detecting and alleviating reduced cognitive function of a pilot of claim 13 wherein the flash generator emits a flash of light after the pupillometer detects reduced cognitive function of the pilot wherein the pupillometer again monitors the pupil response so as to confirm the reduced cognitive function of the pilot.

\* \* \* \* \*